US009927417B2

United States Patent
Yakovlev et al.

(10) Patent No.: US 9,927,417 B2
(45) Date of Patent: Mar. 27, 2018

(54) HIGH REFLECTIVITY INTEGRATING CAVITY AND OPTICAL AMPLIFICATION DEVICE

(71) Applicant: The Texas A&M University System, College Station, TX (US)

(72) Inventors: Vladislav Victorovich Yakovlev, College Station, TX (US); Edward S. Fry, College Station, TX (US); John David Mason, College Station, TX (US); Joel Nathan Bixler, San Antonio, TX (US); Michael Thomas Cone, Houston, TX (US); Brett Harrison Hokr, Bryan, TX (US)

(73) Assignee: The Texas A&M University System, College Station, TX (US)

(*) Notice: Subject to any disclaimer, the term of this patent is extended or adjusted under 35 U.S.C. 154(b) by 91 days.

(21) Appl. No.: 15/001,238

(22) Filed: Jan. 20, 2016

(65) Prior Publication Data

US 2016/0209388 A1 Jul. 21, 2016

Related U.S. Application Data

(60) Provisional application No. 62/104,690, filed on Jan. 16, 2015.

(51) Int. Cl.
*G01N 21/25* (2006.01)
*G01N 33/18* (2006.01)
(Continued)

(52) U.S. Cl.
CPC ......... *G01N 33/1826* (2013.01); *G01N 21/39* (2013.01); *G01N 21/645* (2013.01);
(Continued)

(58) Field of Classification Search
CPC .. G01N 33/1826; G01N 12/39; G01N 12/645; G01N 2021/6469; G01N 2201/065; G01N 2201/0697
(Continued)

(56) References Cited

U.S. PATENT DOCUMENTS 6,515,743 B1 * 2/2003 Hayashi ............. G01N 21/6452
250/458.1
6,626,052 B1 * 9/2003 Martin ................. G01N 17/004
250/228
(Continued)

OTHER PUBLICATIONS

Bixler et al., Ultrasensitive detection of waste products in water using fluorescence emission cavity-enhanced spectroscopy, vol. 111 (20), pp. 7208-7211 (2014).

*Primary Examiner* — Hina F Ayub
(74) *Attorney, Agent, or Firm* — Winstead PC

(57) ABSTRACT

Disclosed is a high reflectivity integrating cavity and device to amplify and detect luminescent emissions produced by small concentrations of materials to be analyzed. Femto or nano molar concentrations of a material can be placed within the high reflectivity integrating cavity. At least the interior surface of the high reflectivity integrating cavity can comprise a coating that, at a designated wavelength of electromagnetic radiation, is transparent and non-absorbing to such designated wavelengths of electromagnetic radiation. In addition to the isotropic field induced by the interior surface of the high reflectivity integrating cavity, the high reflectivity of the interior surface of the high reflectivity integrating cavity leads to very large effective optical path lengths within the interior of the high reflectivity integrating cavity, thereby amplifying the luminescent emissions produced by the sample.

12 Claims, 8 Drawing Sheets

(51) Int. Cl.
*G01N 21/64* (2006.01)
*G01N 21/39* (2006.01)

(52) U.S. Cl.
CPC ............... *G01N 2021/6469* (2013.01); *G01N 2201/065* (2013.01); *G01N 2201/0697* (2013.01)

(58) Field of Classification Search
USPC .......................................................... 356/417
See application file for complete search history.

(56) References Cited

U.S. PATENT DOCUMENTS

| | | | |
|---|---|---|---|
| 2006/0197952 A1* | 9/2006 | Chen | G01N 21/658 356/445 |
| 2011/0222062 A1* | 9/2011 | Martini | G01N 21/05 356/417 |
| 2017/0059740 A1* | 3/2017 | Perkins | G01N 9/00 |

* cited by examiner

HIGH REFLECTIVITY INTEGRATING CAVITY AND OPTICAL AMPLIFICATION DEVICE

CROSS REFERENCES TO RELATED APPLICATIONS

This application claims the benefit under 35 U.S.C. § 119(e) of U.S. Provisional Patent Application No. 62/104,690, filed Jan. 16, 2015, which is incorporated herein by reference in its entirety as if fully set forth herein.

STATEMENT REGARDING FEDERALLY-SPONSORED RESEARCH OR DEVELOPMENT

This invention was made with government support under Grant No. ECCS 0925950 awarded by The National Science Foundation. The government has certain rights in the invention.

TECHNICAL FIELD

The present disclosure relates to a device and method to amplify any luminescent emission process including, without limitation, Raman and fluorescent signals emitted by molecules under investigation to accurately identify these molecules. In particular, the disclosure relates to a high reflectivity integrating cavity that is coupled with optoelectronic devices to form a device that amplifies any luminescent emission process including, without limitation, Raman and fluorescent signals emitted by materials introduced into the interior of the high reflectivity integrating cavity.

BACKGROUND

It is axiomatic that the quality of water is essential for human health. The increasing worldwide contamination of freshwater systems with thousands of industrial and natural chemical compounds is one of the key environmental problems facing humanity today, where pathogens in water cause more than 2 million deaths annually. With more than one-third of the accessible and renewable freshwater used for industrial, agricultural, and domestic applications, pollution from these activities leaves water sources contaminated with numerous synthetic and geogenic compounds. In addition, natural disasters can result in large-scale disruptions of infrastructure, resulting in compromised water quality. Diarrheal disease caused from such disasters may be a major contributor to overall morbidity and mortality rates. Thus, the cleanliness and safety of public water sources has prompted researchers to look for rapid and sensitive indicators of water quality. Whereas most water filtering systems are quite efficient in removing large-size contaminants, smaller particles frequently pass through. These contaminants are often poorly soluble in water and present in quantities of less than 1 nM.

Modern analytical tools have become extremely efficient in the detection and analysis of chemical compounds. For example, liquid chromatography coupled with detection by tandem mass spectrometry has been used for detection of trace pharmaceuticals and other wastewater-derived micropollutants. Although such methods are very powerful in identifying trace pollutants, cost prohibits their widespread use by environmental researchers and, most importantly, prevents real-time analysis of water quality. Other techniques using bench top gas chromatography-mass spectrometry have also been demonstrated as viable methods for detection of basic pharmaceuticals with reduced cost. Despite this, these methods are still cost prohibitive, can hardly be used in field studies, and are unlikely to ever be used for real-time quality control.

In addition to pharmaceutical and other synthetic pollutants such as pesticides, animal and human waste (e.g., feces and urine) are an enormous source of water contamination that can be found in both recreational and source waters. These discarded wastes, when released into water, can carry a variety of diseases such as polio, typhoid, and cholera. In extreme cases pollution of an ecosystem can result in environmental crises, such as, for example, devastation to the aquatic population, red-tide blooms, as well as beach closings. Molecular methods based on polymerase chain reactions are commonly used to monitor viral, bacterial, and protozoan pathogens in wastewater. Microbiological indicators such as fecal coliforms, *Escherichia coli*, and Etherococci are indicators most commonly used to analyze and evaluate the level of fecal contamination. However, the suitability of these indicators has been questioned, and it takes a substantial amount of time from the extraction of a water sample for analysis to the moment when results are ready.

An alternative indicator that has been shown to be helpful in detection of waste in water supplies is urobilin. Urobilin is one of the final byproducts of hemoglobin metabolism, and is excreted in both the urine and feces of many mammals, including humans and common livestock (e.g., cows, horses, and pigs). In addition, as urobilin can be indicative of disease such as hepatic dysfunction or jaundice, an ultrasensitive technique for detection and quantification of this biomarker in solution has both diagnostic and environmental applications.

Urobilin detection in solution has previously been demonstrated using the formation of a phosphor group from the combination of urobilins and zinc ions. Normal heme catabolism results in the production of bilirubin, a red product, which is then broken down into two end products, stercobilin, the bile pigment found in fecal material, and urobilin, the yellow pigment found in urine. Both urobilin and stercobilin have been shown to be viable biomarkers for detection of fecal pollution levels in rivers.

Fluorescent detection of urobilin in urine has been demonstrated based on Schlesinger's reaction in which an urobilinogen-zinc chelation complex exhibits a characteristic green fluorescence when excited by blue light. Methods for detection of urobilinoids using high-performance liquid chromatography with a reversed-phase column and an ultraviolet detector have also been presented; however, the initial sensitivity of this method proved insufficient for clinical analysis. An increase in detection sensitivity of this methodology has been reported, but only to detection levels of 1.5 nM, where efficient excitation and collection of the fluorescent signal remained the limiting factor.

Traditional epiillumination fluorescence spectroscopy systems use an objective lens to focus excitation light into the sample and collect the fluorescence emission. In such a configuration, the signal generated is limited to the focal volume of the optics. In addition, the generated signal is diffusive in nature; only a small fraction of the total emitted light is collected. Because only a small volume of a sample can be probed at any given time with such a configuration, detection of subnanomolar concentrations remains difficult as these measurements are akin to single molecule detection. Thus, a method that could allow for probing a larger volume of a sample while also providing means for collecting more of the fluorescence emission could greatly enhance the ability to detect subnanomolar concentrations of urobilin.

SUMMARY

In one aspect, the present disclosure relates to a high reflectivity integrating cavity. The high reflectivity integrating cavity is comprised of a material such that the interior surface of the high reflectivity integrating cavity exhibits Lambertian behavior. Hence, when electromagnetic radiation of a designated wavelength strikes an interior surface of the high reflectivity integrating cavity, an isotropic field is generated within the high reflectivity integrating cavity. This isotropic field allows for luminescent emission of a large proportion of any sample placed within the high reflectivity integrating cavity. Such luminescent emission can include Raman and fluorescent emissions. Additionally, the high reflectivity integrating cavity enhances the luminescent emission signal strength of the sample to be analyzed by providing long path lengths within the sample region of the high reflectivity integrating cavity.

In another aspect, the disclosure relates to a device. The device comprises the disclosed high reflectivity integrating cavity. Electromagnetic radiation of a designated wavelength can be introduced into the high reflectivity integrating cavity through a port or optical fiber coupled to the high reflectivity integrating cavity. In some embodiments, the same port or optical fiber can be used to sample the luminescent emission emanating from the interior of the high reflectivity integrating cavity. In other embodiments, an output port or optical fiber can be used to sample the luminescent emissions emanating from the interior of the high reflectivity integrating cavity. A detector can be coupled to the port or optical fiber used to sample the luminescent emissions emanating from the interior of the high reflectivity integrating cavity. The detector, in some embodiments, can be a photomultiplier tube. Data collected from the detector can be used to characterize a sample within the high reflectivity integrating cavity.

Moreover, at least the interior surfaces of the high reflectivity integrating cavity can be comprised of materials that exhibit Lambertian behavior when struck by electromagnetic radiation of a designated wavelength. In particular, the interior surfaces of the high reflectivity integrating cavity can be comprised of any material that, at a designated wavelength of radiation, is transparent and non-absorbing and has a different index of refraction than air. Materials that exhibit such properties include fumed silica, quartz powder, gold, and silver as non-limiting examples.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of embodiments of the disclosure and do not limit the disclosure.

DETAILED DESCRIPTION

As used herein, the terms "light" and "electromagnetic radiation" are used interchangeably. The term electromagnetic radiation is intended to refer to any electromagnetic radiation, i.e., including but not limited, to infrared, ultraviolet, microwave, and X-ray radiation.

Figure 1:
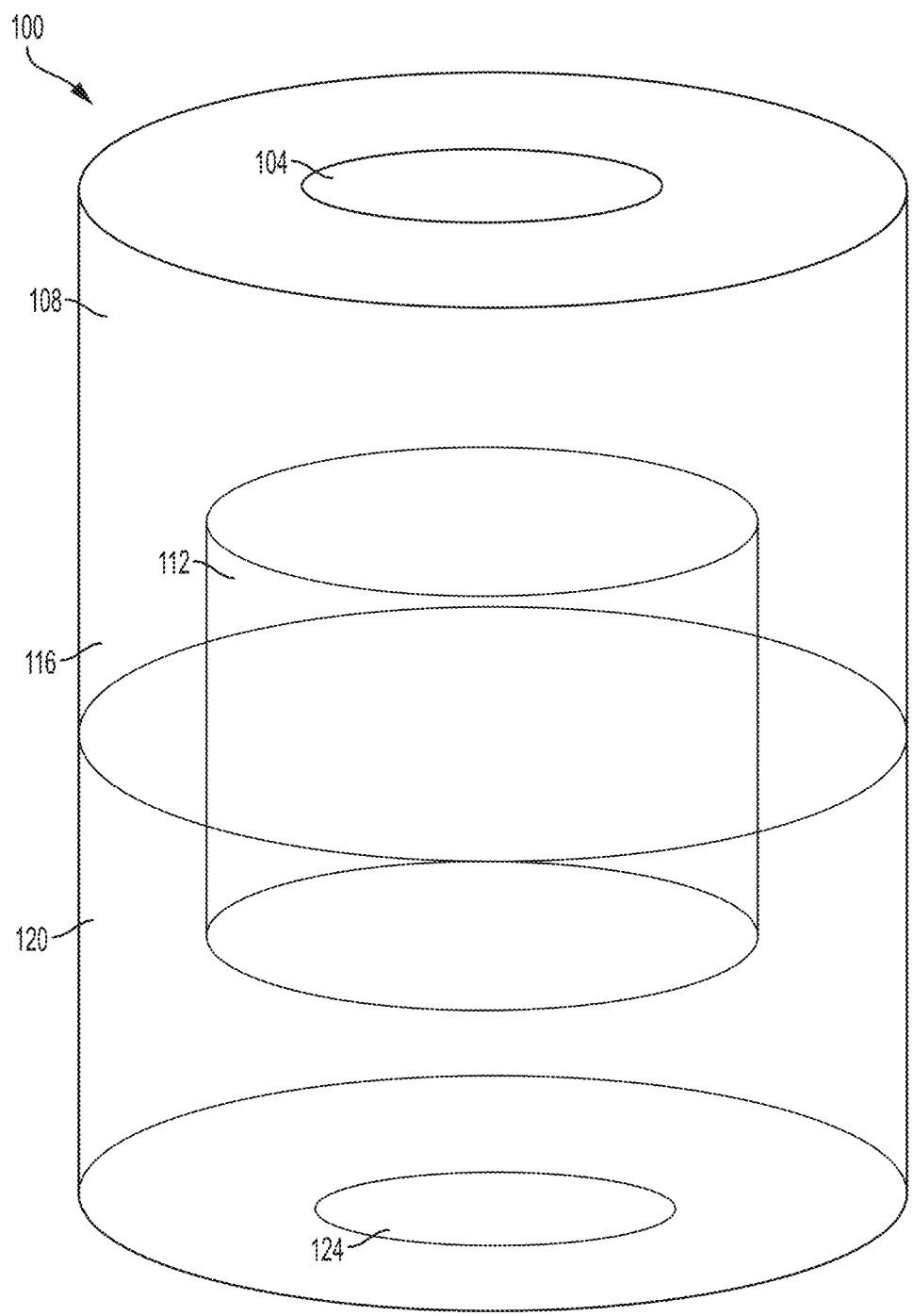
FIG. 1 is a conceptual drawing of an embodiment of the disclosed high reflectivity integrating cavity.

FIG. 1 is a conceptual diagram of an embodiment of an apparatus 100 that includes a high reflectivity integrating cavity 101. The high reflectivity integrating cavity 101 can include an input aperture 104 through which electromagnetic radiation enters. For example, laser light can be shone through the aperture 104. The high reflectivity integrating cavity 101 has a diffuse reflecting surface 108 that optimizes isotropic reflectance of radiation that enters the aperture 104. In particular, a surface exhibits isotropic reflectance if the reflectance is identical from any perspective within the high reflectivity integrating cavity 101. The diffuse reflecting surface 108 can be comprised of any material that exhibits isotropic reflectance at desired wavelengths. More particularly, the diffuse reflecting surface 108 can be comprised of materials that are transparent and non-absorbing at the designated wavelength and that have an index of refraction that is different than air. For example, embodiments of the high reflectivity integrating cavity 101 can include diffuse reflecting surfaces 108 that can be comprised of one or more of packed fumed silica, quartz powder, gold, silver, and porous gallium phosphide. In some embodiments, the packed fumed silica, quartz powder, gold, silver, and porous gallium phosphide may be applied to the diffuse reflecting surfaces 108 as a layer of nanoparticles. The high reflectivity integrating cavity 101 can include a specimen container 112, which can hold a material to be examined. In some embodiments, the high reflectivity integrating cavity 101 can be comprised of two parts, a first part 116 and a second part 120, such that the first part 116 and the second part 120 completely encompass the specimen container 112 when the first part 116 is adjoined to the second part 120. The high reflectivity integrating cavity 101 can include an output aperture 124 through which electromagnetic radiation emanates after the electromagnetic radiation has interacted with the material in the specimen container 112. However, in other embodiments, the high reflectivity integrating cavity 101 may include a single aperture that serves as both an input for electromagnetic radiation and an as an output for electromagnetic radiation.

Although FIG. 1 depicts a high reflectivity integrating cavity 101 with a cylindrical geometry, other geometries are possible. For example, a high reflectivity integrating cavity 101 can have a spherical geometry. Regardless of the geometry of the high reflectivity integrating cavity 101, the Lambertian behavior of the diffuse reflecting walls 108 of the high reflectivity integrating cavity 101 creates an isotropic field within the high reflectivity integrating cavity 101, thereby eliminating the effects of scattering of the sample contained within the specimen container 112. Hence, the output signal emanating from the second aperture 124 is amplified. In particular, the high reflectivity integrating cavity 101 can amplify the output luminescent emission signals emitted by molecules or atoms of a sample contained within the specimen container 112. Additionally, in some configurations, the high reflectivity integrating cavity 101 may lack a specimen container 112.

Figure 2:
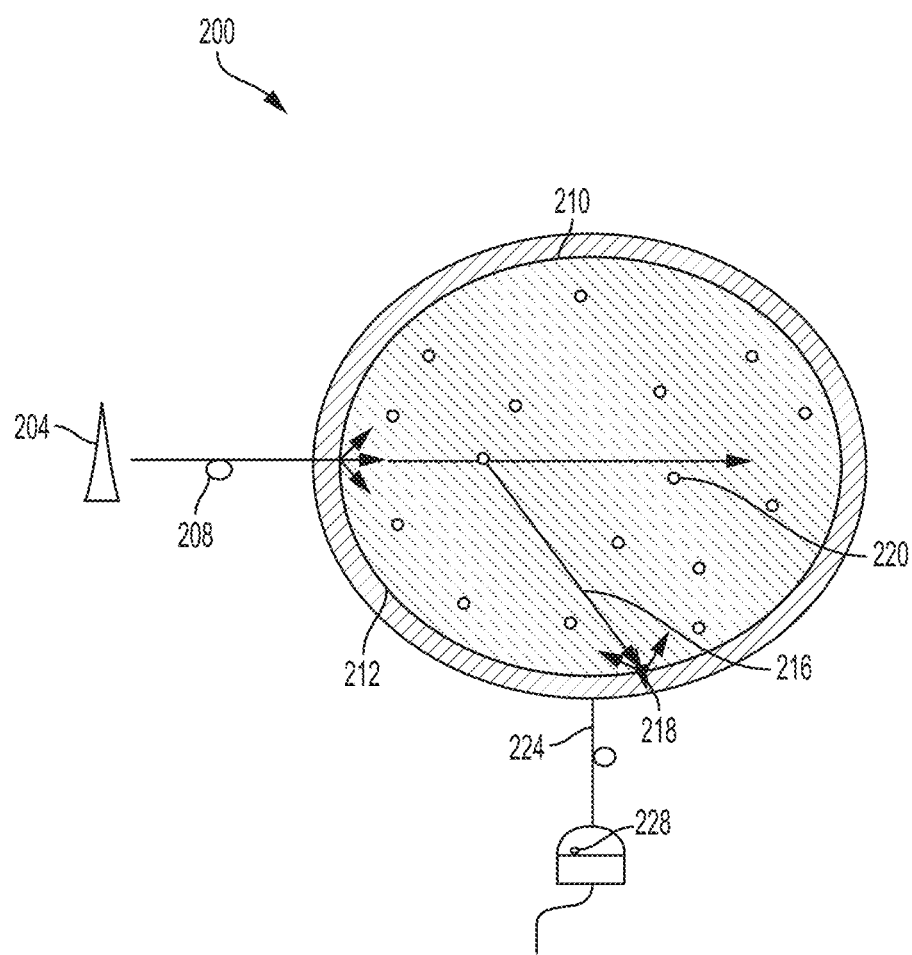
FIG. 2 is a conceptual drawing of an embodiment of the disclosed device as configured to amplify signals emitted by a sample.

FIG. 2 is a conceptual drawing that depicts an embodiment of a device 200 that incorporates a high reflectivity integrating cavity 212 to amplify output signals generated from the interaction of electromagnetic radiation with atoms or molecules of a sample to be analyzed. In one embodiment, the device 200 can include an input optical fiber 208, the high reflectivity integrating cavity 212, an output optical fiber 224, and a photomultiplier tube/detector 228. The high reflectivity integrating cavity 212 is comprised of a diffuse reflecting surface 210. The diffuse reflecting surface 210 exhibits Lambertian behavior, thereby creating an isotropic field within the high reflectivity integrating cavity 212, allowing for luminescent emission excitation of a substantial part of the volume of any sample placed within the high reflectivity integrating cavity 212. Additionally, the high reflectivity of the diffuse reflecting surface 210 leads to a large effective optical path length within the high reflectivity integrating cavity 212.

The input optical fiber 208 is coupled to the high reflectivity integrating cavity 212. The high reflectivity integrating cavity 212 is coupled to the output optical fiber 224. The output optical fiber 224 is coupled to the detector 228. In some embodiments, the detector 228 comprises a photomultiplier tube. The input optical fiber 208 can be configured to receive an input electromagnetic radiation pulse 204. The input electromagnetic radiation pulse 204 enters the high reflectivity integrating cavity 212, where it can interact with a specimen material 220. The output signal 216 generated from the interaction of the input electromagnetic radiation pulse 204 and the specimen material 220 can reflect 218 from the diffuse reflecting surface 210. When photons strike the diffuse reflecting surface 210, a small fraction may scatter directly back into the high reflectivity integrating cavity 212 where they may interact with the specimen material 220, but the majority are likely to penetrate into the diffuse reflecting surface 210. Those photons that penetrate into the diffuse reflecting surface 210 will either reemerge into the high reflectivity integrating cavity 212 through multiple scattering, where these photons may interact with the specimen material 220, or leave the high reflectivity integrating cavity 212 altogether. The detector 228 can be configured to generate an output ring-down pulse. The output ring-down pulse can be used to characterize the specimen material 220.

In other embodiments, the high reflectivity integrating cavity 212 may include a single port through which a single optical fiber is interested. The optical fiber can be used both to deliver a pulse of electromagnetic radiation at a designated wavelength into the high reflectivity integrating cavity 212 and to receive luminescent emission spectra that arise from the interaction of the input electromagnetic radiation signal with sample materials located within the high reflectivity integrating cavity 212.

The diffuse reflecting surfaces 108 and 210 can be comprised of various materials. In particular, the diffuse reflecting surfaces 108 and 210 can be comprised of any materials that, for selected input wavelengths of electromagnetic radiation, are transparent and non-absorbing and that have a different index of refraction from air. In particular, materials are selected that have wide band gaps, refractive index mismatches, and that exhibit an ordered nanostructure, all characteristics that enable a surface to exhibit Lambertian behavior. In some embodiments, a diffuse reflecting surface (e.g., diffuse reflecting surfaces 108 and 210) can be comprised of porous gallium phosphide. In one embodiment, the porous gallium phosphide can be engineered to have a pore size of approximately 0.5 µm to correspond to the 532 nm wavelength of light that could be used as the input wavelength of electromagnetic radiation in an embodiment of the disclosed device. Coupled with the 0.5 µm and the high refractive index of 3.4, the porous gallium phosphide surface is a diffuse reflecting surface for 532 nm light. In another embodiment, silver nanoparticles can be deposited onto the surface of the high reflectivity integrating cavity to form a diffuse reflecting surface 108, 210.

In some embodiments, a diffuse reflecting surface (e.g., diffuse reflecting surfaces 108 and 210) can be comprised of silver nanoparticles. In some embodiments, fumed silica can be used to form the diffuse reflecting surfaces 108 and 210. In some embodiments, silicon can be used to form the diffuse reflecting surfaces 108 and 210.

Embodiments of the disclosed device have been used to detect femtomolar concentrations of urobilin in water and to determine the absorption coefficients of RPE cells as example applications. Other applications, of course, are possible.

Urobilin Experiment

The reflectivity of a high reflectivity integrating cavity was experimentally determined. A temporally short pulse of electromagnetic radiation was directed into the high reflectivity integrating cavity via an input optical fiber. The exponential decay within the high reflectivity integrating cavity of the temporally short pulse of electromagnetic radiation was measured over time. For an empty high reflectivity integrating cavity, the exponential decay constant may be found using Equation 1 below:

$$\tau = -\frac{1}{\ln(\rho)}\left(\frac{d}{c} + \delta t\right), \quad \text{(Equation 1)}$$

Where c is the speed of electromagnetic radiation, d is the average distance of reflections within the high reflectivity integrating cavity, ρ is the reflectivity of the high reflectivity integrating cavity, and δt accounts for the average "wall time" for each reflection. The average distance of reflections within the high reflectivity integrating cavity, d, can be determined using Equation 2 below:

$$d = 4\frac{V}{S} \quad \text{(Equation 2)}$$

Where V is the volume of the high reflectivity integrating cavity, and S is the surface area within the high reflectivity integrating cavity. The average number of reflections of a given photon within the high reflectivity integrating cavity is given by Equation 3 below:

$$\rho = -\frac{1}{\ln(\rho)} \quad \text{(Equation 3)}$$

Thus, the effective path length L within the high reflectivity integrating cavity is given by Equation 4 below:

$$L = nd = -\frac{4}{\ln(\rho)} \frac{V}{S} \approx \frac{4V}{S(1-\rho)}. \quad \text{(Equation 4)}$$

Figure 3:
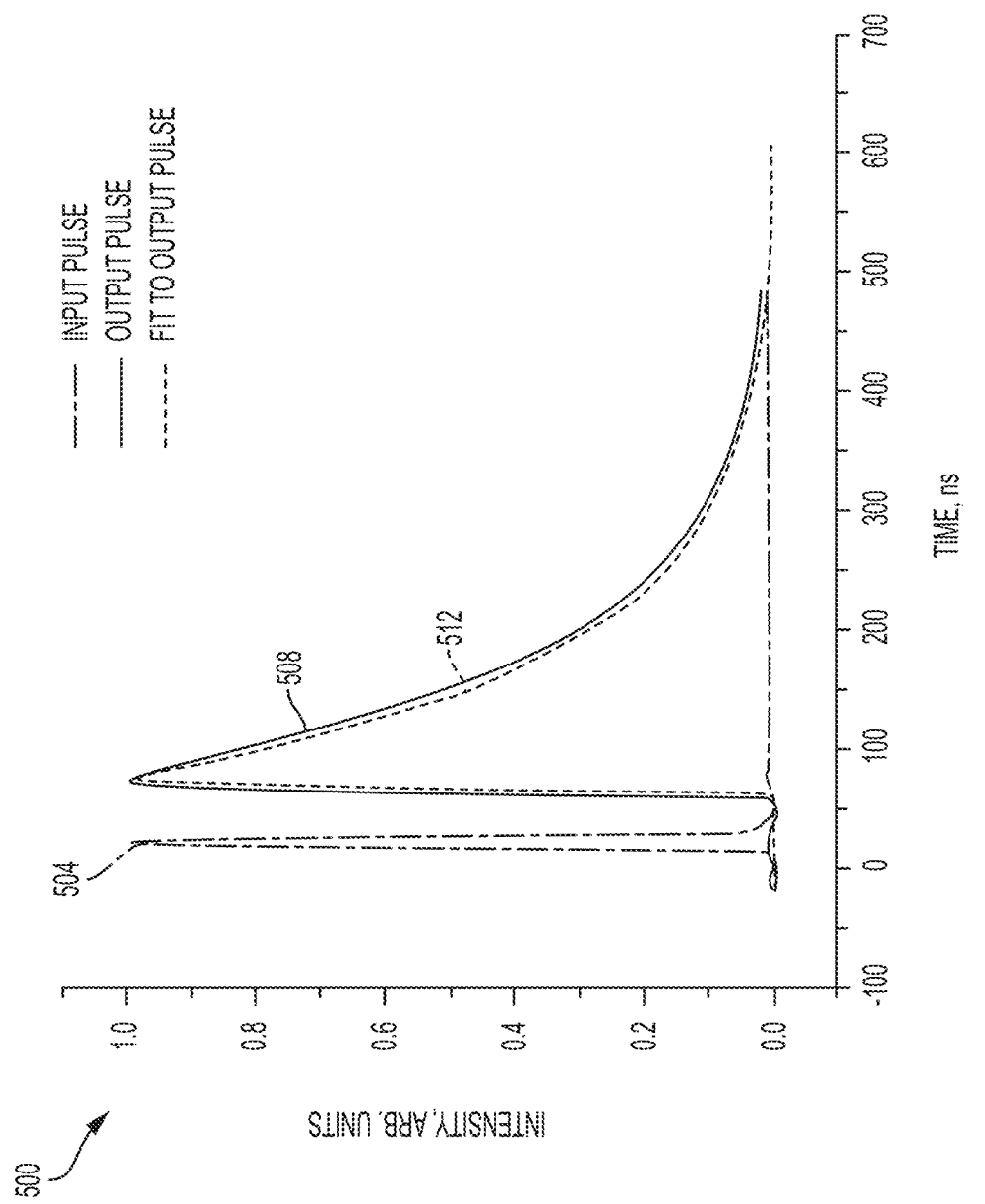
FIG. 3 depicts a ring-down measurement used to determine the reflectance of an embodiment of a high reflectivity integrating cavity.

In the experiment, a 10 ns pulse from a frequency doubled neodymium doped yttrium aluminum garnet laser was introduced into the high reflectivity integrating cavity via an input optical fiber. The decay, or "ring-down" signal, was sampled via an output optical fiber and detected via a photomultiplier tube. FIG. 3 is a graph 500 that depicts results of performing the experiment. In particular, FIG. 3 depicts the input laser pulse 504, the output decay curve 508, and a fit 512 to the output decay curve 508. As shown in FIG. 3, the fit 512 to the output decay curve 508 yielded a decay constant of approximately 98.14 ns. Applying Equation 1, the reflectivity was determined to be 0.9988 at 532 nm. Applying Equation 4, the high reflectivity integrating cavity with a diameter of 50.8 cm had an effective path length L of approximately 30 m for light in the sample region. Hence, the fumed silica high reflectivity integrating cavity overcame the limits of traditional fluorescence spectroscopy because the diffuse scattering of the diffuse reflecting surface of the high reflectivity integrating cavity permitted isotropic illumination of the sample for maximum excitation and the ability to collect the fluorescence signal in $4\pi$ steradians. Additionally, the high reflectivity of the high reflectivity integrating cavity enhanced the fluorescence signal by providing long effective path lengths within the interior of the high reflectivity integrating cavity.

In this experiment, the high reflectivity integrating cavity was formed from fumed silica powder. The fumed silica powder is hydrophilic; therefore, the material was prebaked under a vacuum at a temperature of 250° C. to extract any trapped water. The baked powder was packed into quartz glass shells using a hydraulic press. The packed pieces were baked in a high temperature oven (900° C.-1000° C.) and machined to form the desired high reflectivity integrating cavity geometry. In this experiment, two 11.5 cm quartz rings served as the framework for the high reflectivity integrating cavity. A 5.08 cm diameter bore was machined in each half of the high reflectivity integrating cavity to a depth of 2.54 cm. A small hole of 2.00 mm was added to one of the halves to be used for guiding light into and out of the cavity. The optical setup used a 5 mW light emitting diode (LED) as an excitation source centered at 468 nm. The output of the LED was bandpass filtered to limit its inherently broad spectrum. A 490 nm long-pass filter angled at 45° was used to direct the excitation light to a 20 mm focal length aspheric condenser lens, delivering approximately 420 µW of light into the high reflectivity integrating cavity. The fluorescence emission was collected by the same condenser lens and filtered via a 500 nm long pass filter before being imaged into an Actom 0.300 m CCD spectrometer. A stock solution of urobilin was prepared by dissolving 1.1 mg of urobilin hydrochloride in 20 mL of ethanol. This solution was diluted to a concentration of 1 µM urobilin. Next, 11.25 mg of zinc acetate was added to the solution to permit phosphor formation. Repeating similar steps, samples were prepared from the stock solution, with urobilin concentrations ranging from 100 nM to 500 fM.

Figure 4:
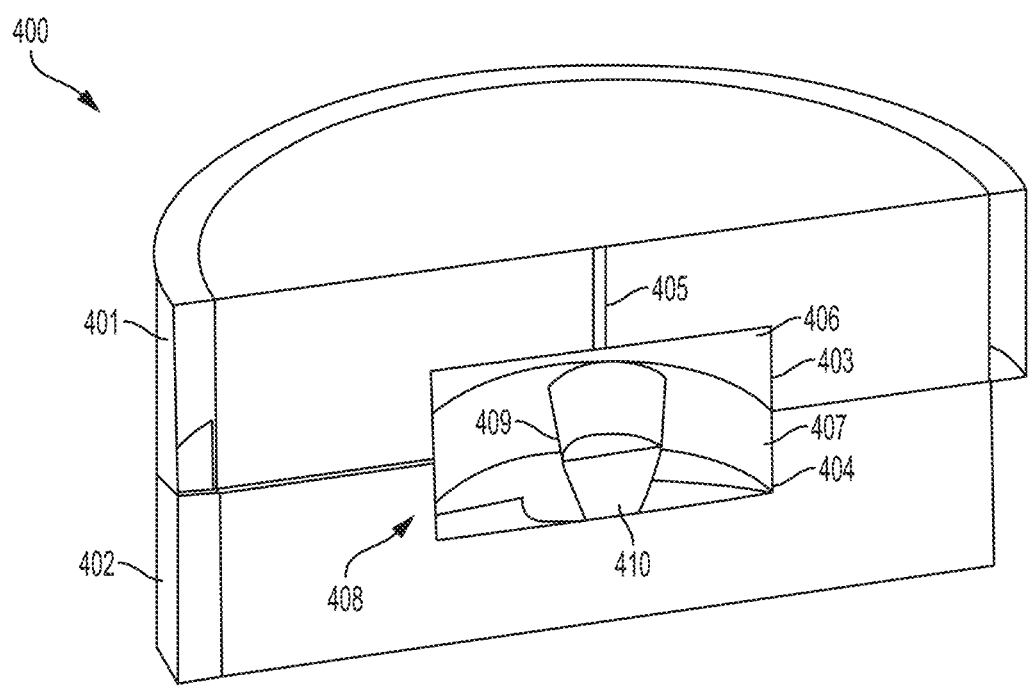
FIG. 4 depicts use of an embodiment of the disclosed device to identify the presence of trace amounts of urobilin in water according to one example.

FIG. 4 depicts an exemplary apparatus 400. The apparatus 400 includes an upper portion 401 and a lower portion 402. The upper and lower portions 401 and 402 may be formed from various materials. As shown in FIG. 4, the upper portion 401 is a cylinder that includes a cavity 403 and an aperture 405. The aperture 405 permits electromagnetic radiation from a source to enter apparatus 400. Electromagnetic radiation sources may include, such as, for example, LED or laser light sources. In some embodiments, the aperture 405 may also serve as an outlet for light to exit the apparatus 400. Light that exits the apparatus 400 may be measured by a detector. In some embodiments, the lower portion 402 may include a second aperture to permit light to exit the apparatus 400.

The cavity 403 may be formed into the upper portion 401 in various ways. For example, in some embodiments the cavity 403 may be formed by boring into the upper portion 401. The aperture 405, which leads from an exterior of the upper portion 401 into the cavity 403, may likewise be formed in various ways, including, for example, drilling through the upper portion 401. In some embodiments, a surface 406 of the cavity 403 comprises a material that provides an isotropic field in the presence of selected wavelengths of light. The material may include fumed silica, quartz powder, gold, and silver as non-limiting examples. The lower portion 402, similar to the upper portion 401, is shown as a cylinder that includes a cavity 404 that aligns with the cavity 403 to define a high reflectivity integrating cavity 408. The cavity 404 includes a surface 407 that is similar to that of the surface 406. The high reflectivity integrating cavity 408 is adapted to house a crucible 409. The crucible 409 may be formed from various materials, such as, for example, quartz, and is adapted to hold a sample 410 for testing.

Figure 5A:
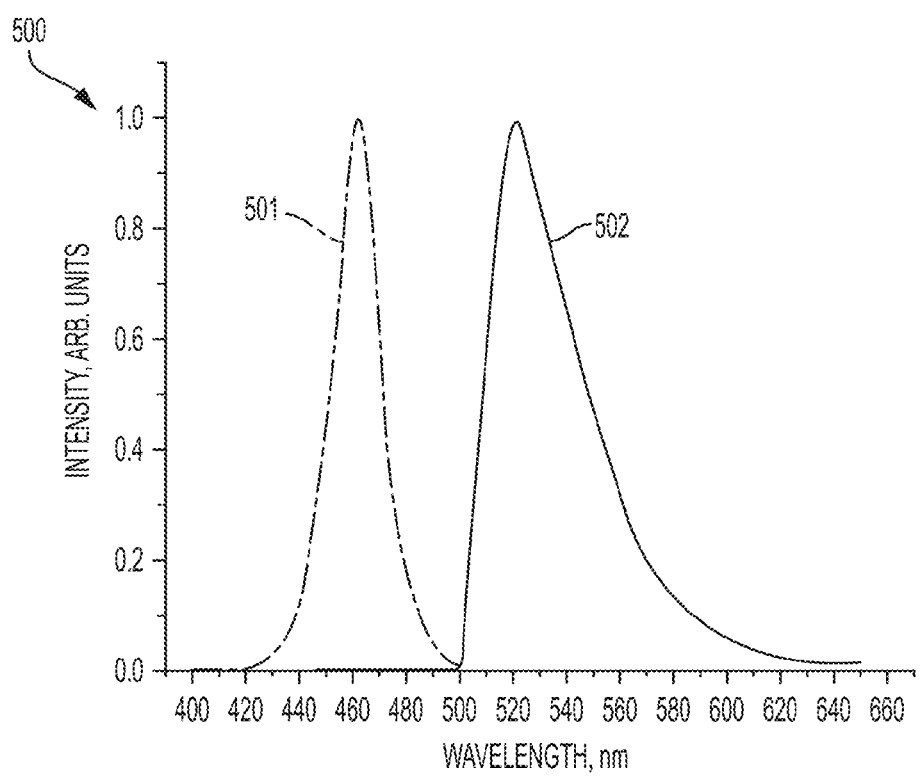
FIG. 5A and FIG. 5B are graphs illustrating certain experimental results obtained from using an embodiment of the disclosed device to detect the presence of trace amounts of urobilin in water.

Fluorescence spectra were recorded for concentrations ranging from 100 nM to 500 fM. Additionally, spectra of the empty high reflectivity integrating cavity and of the ethanol buffer were collected and used for post processing and background removal. Integration times of 100 ms were used for the 100, 10, and 1 nM concentrations, and an integration time of 500 ms was used for all other concentrations. The fluorescence signal was measured for each of the foregoing concentrations. The intensity of each concentration was calculated by integrating the area under the emission curve following removal of the ethanol background. FIG. 5A is a graph 500 showing Intensity versus wavelength in nm. Five spectra were taken for each concentration and averaged. Because spectrometer settings (i.e. integration time) had to be adjusted for lower concentration, the data were corrected to reflect this adjustment. Line 501 shows LED excitation intensity in arbitrary units versus wavelength in nm and line 502 shows urobilin emission intensity in arbitrary units versus wavelength in nm.

Figure 5B:
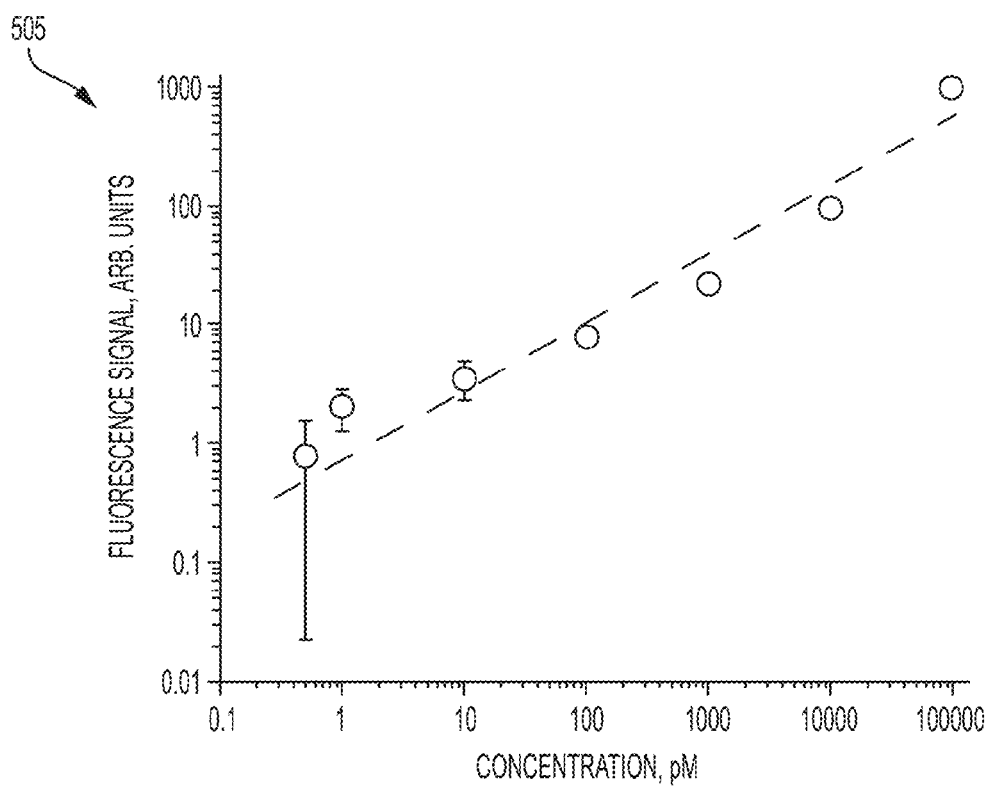

FIG. 5B is a graph 505 showing fluorescence signal in arbitrary units versus concentration in pM. Fluorescence signal easily was detected for urobilin concentrations as low as 500 fM. Even at this concentration, sufficient signal remained to indicate the potential for single femtomolar detection without the need for expensive laser sources. Additionally, measurements can be taken in real time, since integration times below 1 s were sufficient for all samples.

Consequently, the high reflectivity integrating cavity enhanced both the excitation and collection of fluorescence emission from a sample, thereby enabling detection of nM and fM concentrations of urobilin. By placing the sample containing urobilin in a high reflectivity integrating cavity, isotropic illumination enables a fluorescent signal to be generated from the entire volume. The elastic scattering of the diffuse reflecting surface of the high reflectivity integrating cavity limits energy lost within the high reflectivity integrating cavity thus permitting for collection of a larger percentage of the diffuse emission. As empirically demonstrated, significant amplification can be achieved over conventional epiillumination systems even with the use of an inexpensive excitation source such as a single LED.

The foregoing description is offered as an illustrative example of use of the disclosed device for a particular purpose. However, applications of the disclosed device are not limited to detection of a particular compound. In particular, the disclosed device can be used to detect nano and femto molar concentrations of multiple classes of compounds and elements.

Experiment to Measure Optical Absorption Coefficient of RPE Cells

An embodiment of the disclosed device was used in an experiment to measure the optical absorption coefficient of RPE cells. The laser source was a Quanta Ray Pro290 Nd:YAG-pumped VersaScan 355 midband OPO that produced a 6 ns pulse, and was tunable over a range of 412-2550 nm. To prevent detector saturation, the beam was attenuated with a filter wheel before being introduced into the input optical fiber that was used to couple the input pulse into the integrating cavity. An output optical fiber sampled the ring-down signal inside the high reflectivity integrating cavity. This signal was sent to a Thorlabs DET 100 photodiode. An oscilloscope and LabVIEW VI were used to average (typically 50 shots) and record the data.

Samples of the RPE cells were suspended in Dulbecco's phosphate buffered saline (PBS, Mediatech) solution during the Integrated Cavity Ring-Down Spectroscopy ("ICRDS") measurements. The overall sample size for the RPE cell solution was 3 mL, and contained 60 million cells. These samples were pipetted into a quartz crucible which was then placed into a fumed silica high reflectivity integrating cavity. The high reflectivity integrating cavity had a cylindrical inner geometry with a 6.35-cm diameter, and a 6.35-cm height. The RPE cell sample (3 mL) occupied only a small portion of the inner high reflectivity integrating cavity volume. This difference in volume required the use of two samples of known absorption to calibrate the high reflectivity integrating cavity. In addition to these calibration samples, a sample of the PBS solution also had to be measured so that the PBS solution's contribution to the total absorption coefficient of the sample could be subtracted.

In the case of the RPE suspension, the exponential decay constant $\tau_{RPE}$ of the REP suspension is given by Equation 5 below:

$$\tau_{RPE} = \frac{1}{-\ln(\rho) + (a_{pw} + a_D)d_s} \left( \frac{d}{c} + \frac{d_s}{c_s} + \delta t \right) \quad \text{(Equation 5)}$$

Where $d_s$ is the average distance between reflections in the sample, $c_s$ is the speed of light in the sample, d is the average distance between reflections excluding the distance in the sample, c is the speed of light in air, and $a_{PBS}$ and $a_{RPE}$ are absorption coefficients for the PBS buffer and the RPE cells respectively. Similarly, for a solution of pure water and dye, the exponential decay constant is calculated using Equation 6 below:

$$\tau_D = \frac{1}{-\ln(\rho) + (a_{pw} + a_D)d_s} \left( \frac{d}{c} + \frac{d_s}{c_{pw}} + \delta t \right) \quad \text{(Equation 6)}$$

Where $a_{pw}$ is the absorption coefficient of pure water, $a_D$ is the absorption coefficient of the dye, $c_{pw}$ is the speed of light in pure water, and $\delta t$ accounts for the average "wall time" for each reflection. Thus, measuring the decay time for equal volumes of the RPE cell suspension, the PBS buffer and the two dye solutions, applying Equations 5 and 6, the following expression was obtained for the absorption coefficient of the RPE cells:

$$a_{RPE} = \frac{\tau_{RPE}^{-1} - \tau_{PBS}^{-1}}{\tau_{D1}^{-1} - \tau_{D2}^{-1}} (a_{D1} - a_{D2}). \quad \text{(Equation 7)}$$

The foregoing derivation assumes that $c_{pw}$ equals $c_{pbs}$, and this is a reasonable assumption given that the percent difference between the index of refraction for PBS solution and water is less than 1% at 25° C. A solution of ultra-pure water and Irgalan Black, a water soluble organic powder, served as the master dye for these experiments. The two dye solutions used in the measurements were prepared by diluting known amounts of this master dye with additional ultra-pure water. The absorption coefficient of the master dye was determined separately using an Agilent Cary 6000i spectrophotometer, and these data were then used to calculate $a_{D1}$ and $a_{D2}$.

Figure 6:
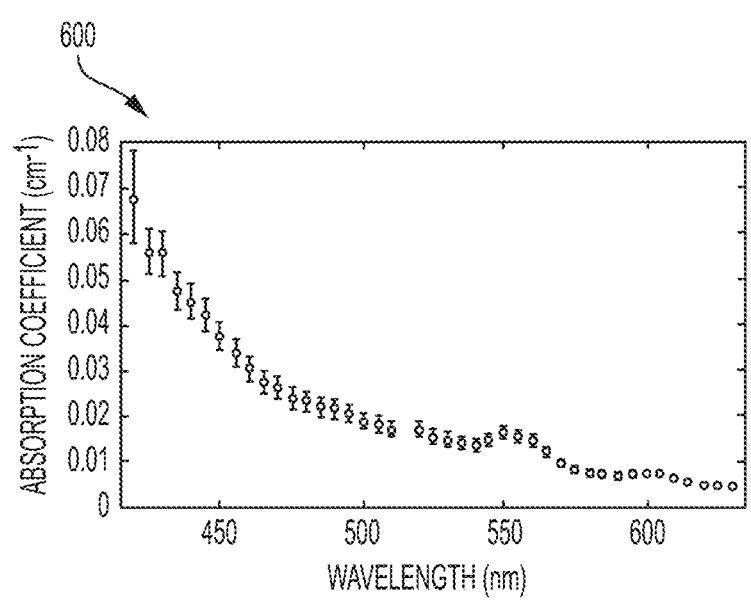
FIG. 6 illustrates certain experimental results obtained from using an embodiment of the disclosed device to determine absorption coefficients of retinal pigmented epithelium (RPE) cells.

FIG. 6 is a graph 600 of absorption coefficient in cm versus wavelength in nm for results of ICRDS measurements of the absorption coefficient from 420-630 nm for a sample containing 60 million RPE cells suspended in PBS solution. The contribution to the absorption coefficient due to the buffer has been subtracted. The data in FIG. 6 shows that the absorption coefficient for the cells drops by more than an order of magnitude as wavelength increases from the visible spectrum to the infrared spectrum. Although the source allowed for tuning from roughly 412-2550 nm, several factors limited this initial study to the region from 420-630 nm.

First, an output signal below 420 nm was too low to be used. This signal issue also occurred at 515 nm, so these data points were excluded from FIG. 6. For the region above 630 nm, the absorption of water starts to dominate. The buffer used (PBS solution) was water based, and thus the majority of the volume of the sample is water. This effect was exacerbated by the fact that the absorption coefficient of the Irgalan black calibrating dye drops off considerably beyond 650 nm. Additionally, it was found that the reflectivity of the fumed silica integrating cavities decreased as the wavelength moved into the infrared. Measurements at 1064 nm give cavity reflectivities of 0.995 (down from as high as 0.9992 at 532 nm). While these factors combined to reduce the wavelength range for this initial work, there are several simple steps that can be taken to expand the range of future experiments. The error bars shown in FIG. 6 result from a combination of the standard error in the least-squares fits, the accuracy of the concentration of the calibrating dye solutions, and the accuracy of the spectrophotometer used to measure the absorption coefficient of the master dye solution. Standard error for the least-squares fits had to be calculated for each sample (i.e. $dt_{RPE}$, $dt_{PBS}$, $dt_{D1}$, and $dt_{D2}$), and propagated in accordance with Equation 5. The calibrating dye solutions were prepared by pipetting small amounts (7 mL 1% for dye 1, and 5 mL 1% for dye 2) of the master dye solution, and then diluting with ultra-pure water to a volume of 250 mL 0.05% in a volumetric flask. An Agilent Cary 6000i spectrophotometer, with a photometric accuracy of 0.0003 absorbance units, was used to measure the absorption coefficient of the master dye solution. The resulting relative uncertainties were less than 10% for the data from 425-625 nm, 15% at 420 nm, and 10% at 630 nm.

Some insight into the advantages of this new ICRDS technique can be obtained by comparing these results with transmission style measurements. To make this comparison, the same sample of RPE cells were taken and pipetted into a 10 mm×10 mm quartz cuvette. An Agilent Cary 6000i spectrophotometer was used to measure the absorbance of the cell sample. A blank of the PBS buffer solution also was measured, and subtracted out.

Figure 7:
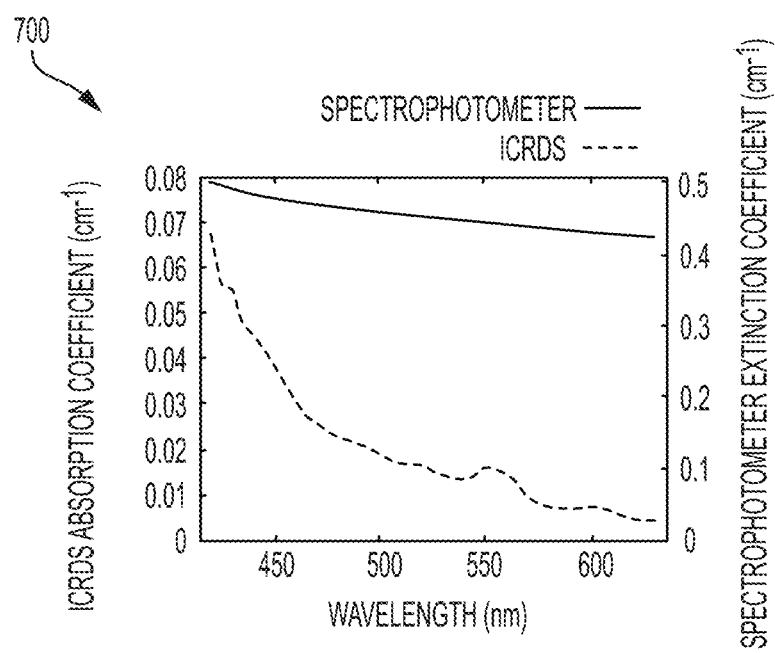
FIG. 7 illustrates a comparison of using an embodiment of the disclosed device to determine absorption coefficients of RPE cells compared to using a standard spectrometer to determine absorption coefficients of the same RPE cells.

FIG. 7 is a graph 700 showing results of spectrophotometer measurements of a sample, along with ICRDS data for the same sample. The ICRDS data clearly shows structure that is not seen in the spectrophotometer data. Additionally, the spectrophotometer data give values that are on average ten times larger than the ICRDS values (note the two vertical scales on FIG. 7). This difference is entirely due to the large losses from scattering in the RPE cell sample. In other words, the spectrophotometer is measuring the attenuation coefficient for the sample, whereas ICRDS is providing a true measurement of the absorption coefficient.

A simple test was performed to verify that the ICRDS technique was insensitive to scattering in the sample. The test involved measuring the decay times for sample suspensions of scattering particles with increasing concentration. The scatterers used were transparent Duke Scientific copolymer microspheres in a 10% w/w water suspension (catalog #: 7508). The microspheres had a mean diameter of 8 microns. Small volumes (1 mL, 3 mL, and 5 mL) of this master suspension were diluted with ultra-pure water to a volume of 500 ml to make three sample suspensions. Three additional samples were prepared using a dilution of the same Irgalan Black master dye used in the ICRDS measurements. The first of these contained only the master dye diluted by a factor of 100 with pure water. The other two samples used the same diluted dye, but also included a small volume of the master scatterer suspension (1 ml and 2 ml of scatters added, respectively).

A ring-down decay constant for a 5 mL sample of each of these suspensions was measured using the 532-nm output of a Continuum Powerlite Precision 9010 Nd:YAG laser (10-ns pulse), and a Hamamatsu 1P21 PMT for detection. Table 1 below shows the results of the ring-down measurements.

TABLE 1

| Ring-Down Measurements | |
|---|---|
| Scatterers (1 ml diluted to 500 ml) | 133.5 |
| Scatterers (3 ml diluted to 500 ml) | 131.5 |
| Scatterers (5 ml diluted to 500 ml) | 133.0 |
| Dye solution (no scatterers) | 89.1 |
| Dye solution + 1 ml scatterers | 89.1 |
| Dye solution + 2 ml scatterers | 87.8 |

The decay constants for the three scattering suspensions remained nearly identical, despite the 5-fold increase in scatterer concentration. The small differences seen (less than 1.5%) are well within the relative uncertainty of the absorption measurements shown above. The addition of the absorbing dye to the solution drops the decay constant from 133.0 ns to 89.1 ns. However, the addition of scatterers to this dye solution produces almost no change to measured decay constant. Again the differences between the various samples were all less than 1.5%.

Figure 8A:
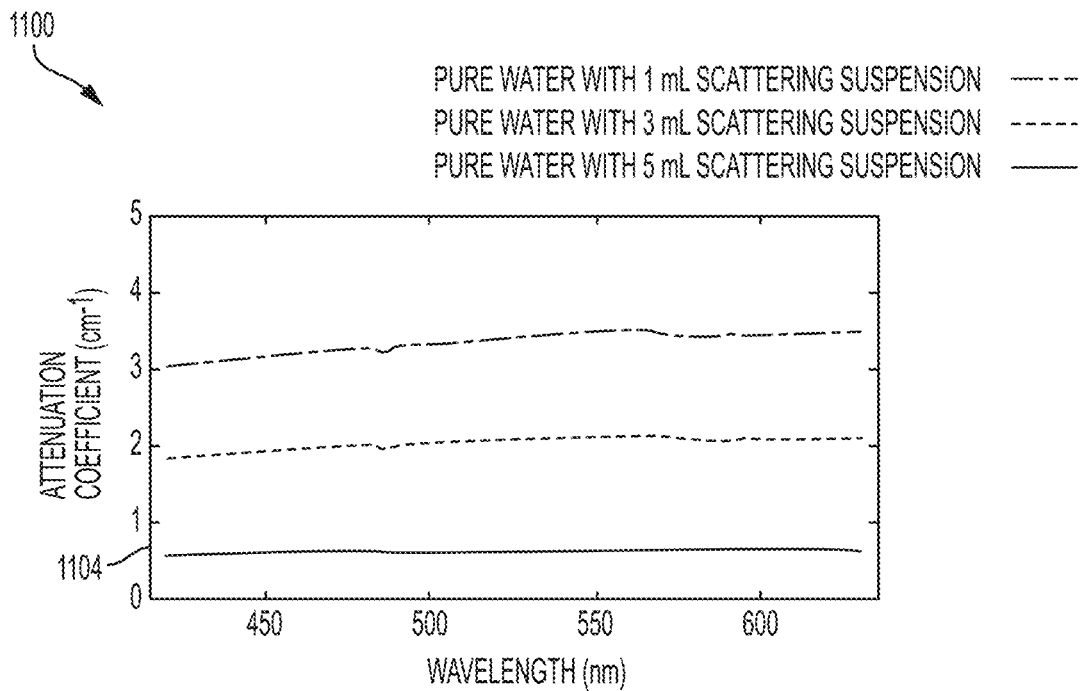
FIG. 8A and FIG. 8B illustrate spectrophotometer measurements of the attenuation coefficient for suspensions of pure water and copolymer microsphere scatterers (FIG. 8A), and the attenuation coefficient for dye solutions with and without scatterers (FIG. 8B).
Figure 8B:
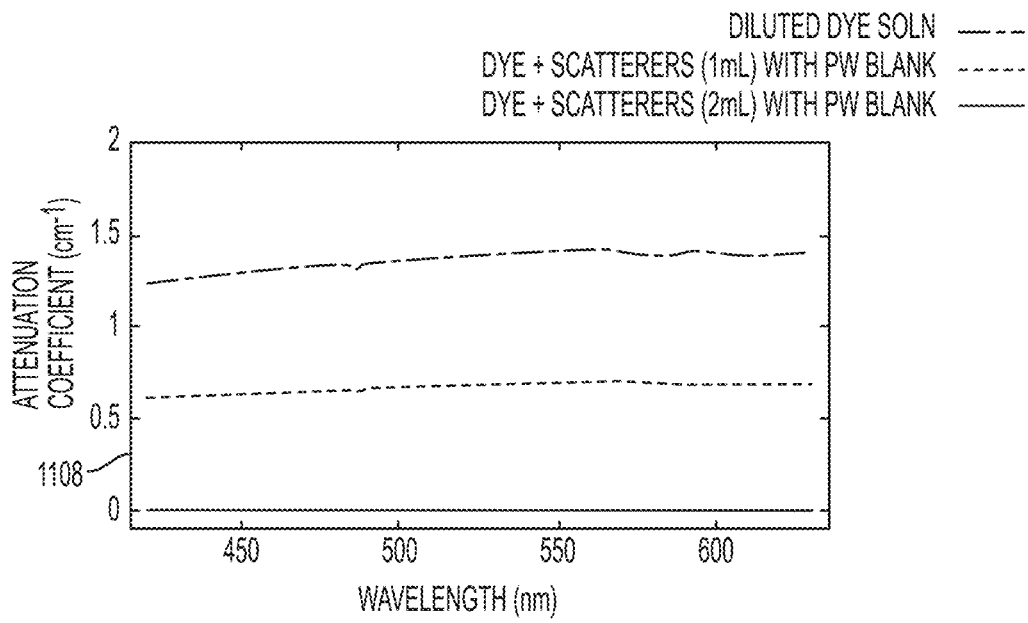

The same set of samples was measured with an Agilent 8453 UV-VIS spectrophotometer. FIGS. 8A and 8B are graphs of measurements taken with the Agilent 8453 UV-VIS spectrophotometer. As shown in FIG. 8A, the measured attenuation (or extinction) coefficient increases proportionally with the increased concentration of scatterers in the sample. As shown in FIG. 8B, a nearly proportional increase in the measured attenuation coefficient with increasing scatterer concentration is observed. In fact, the spectrophotometer gives negative values over much of the visible spectrum for the dye solution without scatterers, indicating that the dye solution is below the detection threshold for the instrument. Comparison of the plots of FIGS. 8A and 8B shows that the scatterers actually dominate the signal, and are responsible for nearly all the measured attenuation for the dye/scatterer solutions.

These results demonstrate the critical importance that scattering plays when making absorption measurements with a transmission-style experiment. ICRDS shows a clear ability to directly measure small absorption coefficients, while simultaneously being insensitive to the effects of scattering in the sample. However, there are limits to the amounts of absorption and scattering (or net attenuation) that can be present before the assumption of an isotropic field throughout the sample region breaks down. Work with other integrating cavity absorption measurement techniques suggests that this assumption only begins to fail when the net attenuation is on the order of the inverse of the high reflectivity integrating cavity dimension. However, it should be noted that the work in these studies considered the case of a cavity filled with the sample. As mentioned in the methods section, the samples used in this work occupied only a small fraction of the total cavity volume. Thus, it is the inverse of this sample dimension that would be relevant in estimating the upper limit for attenuation for a particular sample size.

The experiment demonstrated that ICRDS provides a highly sensitive technique for measuring the absorption coefficient of low-absorbing samples, even in the presence of strong scattering. The results of ICRDS also were compared with spectrophotometer data to demonstrate the need for direct measurements of the absorption coefficient, as opposed to the attenuation coefficient, which is the quantity measured with transmission style experiments. It should be noted that for this work the sample size was extremely small (3 mL total volume), and that larger sample sizes should allow for reduced uncertainty in the measurements. The wavelength range of the measurements could be expanded with some basic adjustments. For instance, using a stronger-absorbing dye above 630 nm would allow for better discrimination between the absorption due to sample, and the absorption due to the water in the buffer solution, and thus allow the measurements to be extended further towards the infrared. Increasing the cell-to-buffer ratio could provide a similar benefit. The integrating cavity itself can also be modified. While the fumed silica powder is an exceptional choice for the ICRDS diffuse reflector in the UV and visible spectra, there is no reason that another material could not be used for other portions of the spectrum. While this work centered on measuring the absorption coefficient for cells suspended in liquid solutions, this technique also could be used to examine absorption in bulk tissue, subcellular constituents, aerosolized particles, or even trace gases.

While this invention has been particularly shown and described with references to example embodiments thereof, it will be understood by those skilled in the art that various changes in form and details may be made therein without departing from the scope of the invention encompassed by the appended claims.

We claim:

1. An apparatus for detecting compounds, the apparatus comprising:
   a high reflectivity integrating cavity formed within the apparatus, the high reflectivity integrating cavity comprising an interior surface comprising a material that exhibits Lambertian behavior thereby generating an isotropic field within the high reflectivity integrating cavity, the isotropic field inducing a spectral emission in a volume of a sample placed within the high reflectivity integrating cavity, further comprising:
      an upper portion with a first cavity formed into a bottom surface of the upper portion and a lower portion with a second cavity formed into an upper surface of the lower portion; and
      wherein when the upper portion and the lower portion are stacked, the first cavity and the second cavity form the high reflectivity integrating cavity.

2. The apparatus of claim 1, wherein at least the interior surface of the high reflectivity integrating cavity includes at least one of packed fumed silica, quartz powder, gold, and silver.

3. The apparatus of claim 2, wherein the packed fumed silica, quartz powder, gold, or silver are deposited on the interior surface as a layer of nanoparticles to enhance scattering of radiation.

4. The apparatus of claim 1, wherein at least the interior surface of the high reflectivity integrating cavity is comprised of a material that, at a designated wavelength of electromagnetic radiation, is transparent and non-absorbing and has a different index of refraction than air.

5. The apparatus of claim 1, wherein the upper portion comprises an aperture formed through an upper surface of the upper portion.

6. The apparatus of claim 5, wherein the lower portion comprises an aperture formed through a bottom surface of the lower portion.

7. The apparatus of claim 6, further comprising:
   a detector adapted to receive a spectral emission emitted by a material within the high reflectivity integrating cavity; and
   wherein the detector, after receiving the spectral emission emitted by a material within the high reflectivity integrating cavity, can identify the material.

8. The apparatus of claim 7, wherein the detector is a photomultiplier tube.

9. The apparatus of claim 5, further comprising an input optical fiber coupled to the apparatus to introduce electromagnetic radiation into the high reflectivity integrating cavity.

10. The apparatus of claim 5, further comprising:
    an optical fiber to introduce light into the high reflectivity integrating cavity via the aperture and to sample an exponential decay of an irradiance on an interior surface of the high reflectivity integrating cavity;
    a detector adapted to receive a spectral emission emitted by a material within the high reflectivity integrating cavity; and
    wherein the detector facilitates identification of the material via the spectral emission.

11. The apparatus of claim 10, wherein the detector is a photomultiplier tube.

12. The apparatus of claim 1, wherein the spectral emission includes a Raman or a fluorescent emission.

* * * * *